United States Patent
Kim et al.

(10) Patent No.: US 12,397,031 B2
(45) Date of Patent: Aug. 26, 2025

(54) *LONICERA JAPONICA* **FLOWER WATER EXTRACT-CONTAINING PHARMACEUTICAL COMPOSITION FOR PREVENTING OR TREATING *HELICOBACTER PYLORI* INFECTION**

(71) Applicant: GREEN CROSS WELLBEING CORPORATION, Seoul (KR)

(72) Inventors: Jeom Yong Kim, Seongnam-si (KR); Sun Kyu Park, Seongnam-si (KR); Min Jung Jang, Seongnam-si (KR); Jong Hoon Lee, Seongnam-si (KR); Su Hwan Lim, Seongnam-si (KR)

(73) Assignee: Green Cross Wellbeing Corporation, Seoul (KR)

( * ) Notice: Subject to any disclaimer, the term of this patent is extended or adjusted under 35 U.S.C. 154(b) by 1064 days.

(21) Appl. No.: 17/299,893

(22) PCT Filed: Nov. 29, 2019

(86) PCT No.: PCT/KR2019/016671
§ 371 (c)(1),
(2) Date: Jun. 4, 2021

(87) PCT Pub. No.: WO2020/116862
PCT Pub. Date: Jun. 11, 2020

(65) Prior Publication Data
US 2022/0023366 A1    Jan. 27, 2022

(30) Foreign Application Priority Data
Dec. 6, 2018    (KR) .................... 10-2018-0155638

(51) Int. Cl.
*A61K 36/355*    (2006.01)
*A23L 2/52*    (2006.01)
(Continued)

(52) U.S. Cl.
CPC .............. *A61K 36/355* (2013.01); *A23L 2/52* (2013.01); *A23L 33/105* (2016.08); *A23P 10/28* (2016.08);
(Continued)

(58) Field of Classification Search
None
See application file for complete search history.

(56) References Cited

U.S. PATENT DOCUMENTS 9,662,366 B2    5/2017  Shraibom
2007/0111955 A1    5/2007  Kwak et al.
(Continued)

FOREIGN PATENT DOCUMENTS

CN    105435202 A    3/2016
CN    105640975 A    6/2016
(Continued)

OTHER PUBLICATIONS

Ju Yup Lee, et al., "No Correlation of Inflammation With Colonization of Helicobacter pylori in the Stomach of Mice Fed High-salt Diet", Journal of Cancer Prevention, Jun. 2014, pp. 144-151, vol. 19, No. 2.
(Continued)

*Primary Examiner* — Lakshmi S Channavajjala
(74) *Attorney, Agent, or Firm* — Sughrue Mion, PLLC

(57) ABSTRACT

The present invention pertains to a *Lonicera japonica* flower water extract composition for preventing or treating *Helicobacter pylori* infection, the composition containing secoxyloganin as an active ingredient. The extract contains a specific amount of secoxyloganin, and thus exhibited excellent antibacterial effects when used on *Helicobacter pylori* bacteria, and exhibited excellent effects in terms of reducing *Helicobacter pylori* IgG antibody expression in the blood, alleviating histopathological lesions, and reducing (Continued)

cytokine expression when used on *Helicobacter pylori*-infected mice. Thus, the *Lonicera japonica* flower water extract of the present invention can be usefully used as a composition for preventing or treating *Helicobacter pylori* infection.

4 Claims, 7 Drawing Sheets

Specification includes a Sequence Listing.

(51) Int. Cl.
*A23L 33/105* (2016.01)
*A23P 10/28* (2016.01)
*A23P 10/30* (2016.01)
*A61K 31/7048* (2006.01)
*A61P 1/04* (2006.01)
*A61P 31/04* (2006.01)

(52) U.S. Cl.
CPC .......... *A23P 10/30* (2016.08); *A61K 31/7048* (2013.01); *A61P 31/04* (2018.01); *A23V 2002/00* (2013.01)

(56) References Cited

U.S. PATENT DOCUMENTS

| | | |
|---|---|---|
| 2009/0163551 A1 | 6/2009 | Earnest |
| 2013/0310454 A1 | 11/2013 | Yoo et al. |
| 2016/0136218 A1 | 5/2016 | Shraibom |

FOREIGN PATENT DOCUMENTS

| | | |
|---|---|---|
| CN | 105939721 A | 9/2016 |
| CN | 106421612 A | 2/2017 |
| JP | 2007-077117 A | 3/2007 |
| JP | 2007-197386 A | 8/2007 |
| KR | 10-0526629 B1 | 11/2005 |
| KR | 10-2006-0040254 A | 5/2006 |
| KR | 10-0878436 B1 | 1/2009 |
| KR | 10-2016-0114206 A | 10/2016 |
| WO | 2009/132888 A1 | 11/2009 |
| WO | 2010/083968 A1 | 7/2010 |
| WO | 2011/071296 A2 | 6/2011 |
| WO | 2012/105798 A2 | 8/2012 |

OTHER PUBLICATIONS

Feng Ma, et al., "Screening test for anti-Helicobacter pylori activity of traditional Chinese herbal medicines", World Journal of Gastroenterology, Nov. 28, 2010, pp. 5629-5634, vol. 16, Issue 44.

Hisae Oku, et al., "Allergy-Preventive Effects of Chlorogenic Acid and Iridoid Derivatives from Flower Buds of Lonicera japonica", Biol. Pharm. Bull., Pharmaceutical Society of Japan, 2011, pp. 1330-1333, vol. 34, No. 8.

Zhu-Ping Xiao, et al., "Molecular Docking, Kinetics Study, and Structure-Activity Relationship Analysis of Quercetin and Its Analogous as Helicobacter pylori Urease Inhibitors", Journal of Agricultural and Food Chemistry, ACS Publications, American Chemical Society, 2012, pp. 10572-10577, vol. 60, No. 42.

Jianhua Xiong, et al., "Screening and identification of the antibacterial bioactive compounds from *Lonicera japonica* Thunb. leaves", Food Chemistry, 2013, pp. 327-333, vo. 138.

Hyun-A Lee, et al., "Study on the antimicrobial activities of herbal extracts against Helicobacter pylori", Korean J Vet Res, 2013, pp. 117-123, vol. 53, No. 2.

Dan Tang, et al., "Rapid and simple method for screening of natural antioxidants from Chinese herb Flos Lonicerae Japonicae by DPPH-HPLC-DAD-TOF/MS", Journal of Separation Science, 2008, pp. 3519-3526, vol. 31.

Sae-Kwang Ku, et al., "Effect of Lonicerae Flos extracts on reflux esophagitis with antioxidant activity", World Journal of Gastroenterology, Oct. 14, 2009, pp. 4799-4805, vol. 15, No. 38.

Byung-Il Lee, et al., "Anti-ulcerogenic Effect and HPLC Analysis of the Caffeoylquinic Acid-Rich Extract from Ligularia stenocephala", Biological & Pharmaceutical Bulletin, Mar. 2010, pp. 493-497, vol. 33, No. 3.

Joel J. Heidelbaugh, M.D., et al., "Management of Gastroesophageal Reflux Disease", American Family Physician, Oct. 1, 2003, pp. 1311-1318, vol. 68, No. 7.

International Searching Authority, International Search Report for PCT/KR2019/016671 dated Mar. 10, 2020 (PCT/ISA/210).

Du Pinghua et al., "Antibacterial Activity of 20 Kinds of Chinese Medicinal Materials for Helicobacter Pylori in vitro", Journal of Chinese Medicinal Materials, 2001, vol. 3, pp. 188-189 (4 pages total).

Song Yaling et al., "Isolation of High-Purity Secoxyloganin from Flos Lonicera Japonica by Industrial Dynamic Axial Compression Preparative Chromatography", World Science and Technology-Modernization of Traditional Chinese Medicine, 2016, vol. 18, No. 3, pp. 522-526 (6 pages total).

Jung-Woo Kang et al., "Protective Effect of Flos Lonicerae against Experimental Gastric Ulcers in Rats: Mechanisms of Antioxidant and Anti-Inflammatory Action", Evidence-Based Complementary and Alternative Medicine, 2014, vol. 2014, Article ID No. 596920, pp. 1-11 (12 pages total).

Xiaofei Shang et al., "*Lonicera japonica* Thunb.: Ethnopharmacology, phytochemistry and pharmacology of an important traditional Chinese medicine", Journal of Ethnopharmacology, 2011, vol. 138, pp. 1-21 (21 pages total).

G1 : Normal group (untreated group, D.W)
G2 : Infected group (untreated group, D.W)
G3 : Positive control group 1 (14.25 mg/kg AMX + 7.15 mg/kg CLR + 400 μmol/kg omeprazole)
G4 : Positive control group 2 (60 mg/kg licorice extract)
G5 : Example 1 (100mg/kg)
G6 : Example 1 (200mg/kg)
G7 : Example 1 (400mg/kg)

SEQUENCE LISTING

<160> NUMBER OF SEQ ID NOS: 2

<210> SEQ ID NO 1
<211> LENGTH: 29
<212> TYPE: DNA
<213> ORGANISM: Artificial Sequence
<220> FEATURE:
<223> OTHER INFORMATION: Primer

<400> SEQUENCE: 1
ataatgctaa attagacaac ttgaagcga                               29

<210> SEQ ID NO 2
<211> LENGTH: 28
<212> TYPE: DNA
<213> ORGANISM: Artificial Sequence
<220> FEATURE:
<223> OTHER INFORMATION: primer

<400> SEQUENCE: 2
ttagaataat caacaaacat cacgccat                                28

LONICERA JAPONICA FLOWER WATER EXTRACT-CONTAINING PHARMACEUTICAL COMPOSITION FOR PREVENTING OR TREATING HELICOBACTER PYLORI INFECTION

CROSS REFERENCE TO RELATED APPLICATIONS

This application is a National Stage of International Application No. PCT/KR2019/016671 filed Nov. 29, 2019, claiming priority based on Korean Patent Application No. 10-2018-0155638 filed Dec. 6, 2018.

SEQUENCE LISTING

The content of the electronically submitted sequence listing, file name: Sequence_Listing_As_Filed.txt; size: 767 bytes; and date of creation: Jun. 4, 2021, filed herewith, is incorporated herein by reference in its entirety.

TECHNICAL FIELD

The present invention relates to a pharmaceutical composition for preventing or treating *Helicobacter pylori* infection comprising a *Lonicera japonica* flower water extract.

BACKGROUND ART

*Helicobacter pylori* (H. *Pylori*) was first discovered by Marshall and Warren in Australia in 1983. It was reported that the *Helicobacter pylori* is spiral micro-aerobic gram-negative bacteria with 4 to 6 flagella and is infected to more than half of the world's population, and in Korea, 70% or more of infection rate in adults over 40 years of age has been reported. The *Helicobacter pylori* is mainly known as a causative organism which is closely associated to the upper digestive diseases to cause chronic gastritis, gastric and duodenal ulcer, gastric cancer, etc. Particularly, the International Agency for Research on Cancer (IARC) and the World Health Organization defined *Helicobacter pylori* as Class I carcinogen. Regarding the prevention and diagnosis of gastric cancer, the infection of *Helicobacter Pylori* is accepted as a very important issue, and identifying an infectious factor of *Helicobacter pylori* is being accepted as an important issue for national health.

The *Helicobacter pylori* has 5 to 6 flagella similar to the animal's tail as a locomotive organ and is seated on the surface the gastric mucosal membrane by passing through the sticky mucus directly on the gastric wall by using the flagella. Urease is genetically well preserved between individuals as a common feature that is found in most strains of *Helicobacter pylori*. The urease hydrolyzes urea into ammonia ($NH_3$) and carbon dioxide ($CO_2$) so that bacteria survive in the gastric mucosal membrane having a low pH that the bacteria can not survive to increase surrounding pH and neutralize gastric acid, and then the bacteria survive. The cell destruction and mutation in the gastric mucosal membrane are caused by the influence of the produced ammonia to lose the gastric acid defensive action, and a vicious cycle that attacks the gastric acid to the gastric mucosal membrane is generated, causing gastric tissue change and inflammatory reactions. As such, the gastric mucosal membrane inflammation caused by various cytotoxic factors secreted by *Helicobacter pylori* induces the activation of various inflammatory cells such as lymphocytes and macrophages. It has been reported that the inflammatory cells have an adverse affect in vivo such as tissue damage, cytotoxicity, etc., and induce inflammatory inducing media to deteriorate the inflammation.

The *Helicobacter pylori* is a very dangerous microorganism in gastrointestinal diseases, but the development of proper antimicrobial materials is lack. Currently, as methods for treating *Helicobacter pylori*, there are a general triple therapy of co-treating a bismuth agent, metronidazole, and tetracycline or amoxicillin and a quartet therapy of mixing a bismuth agent, omeprazole, tetracycline, and metronidazole, etc. It has been reported that these treatment methods have an excellent effect of treating *Helicobacter pylori*. However, it has been reported that repeating use of these drugs causes increased antibiotic resistance and various side effects, and currently, efforts are continuing to find extracts and active ingredients capable of suppressing *Helicobacter pylori* using various natural materials.

*Lonicera japonica* flower (Lonicerae Flos) is flower of *Lonicera japonica* Thunb. in the Caprifoliaceae, and has been used for diuresis, strong stomach, arthritis, purulent dermatitis, and bronchitis in the oriental medicine and nonofficial.

It has been reported that as ingredients of the *Lonicera japonica* flower, there are tannin, inositol, sterol, chlorogenic acid, isochlogenic acid, etc., and it has been reported that as flavonoid ingredients, there are luteolin, apigenin, luteolin-7-ramnoglucoside, luteolin-7-O-rhamnoglucoside, quercetin, etc. The flavonoid ingredients of the *Lonicera japonica* Flower have been known to have an anti-inflammatory effect and an antimutagenic effect.

As prior arts related with the composition for preventing or treating *Helicobacter pylori* infection comprising the *Lonicera japonica* flower water extract, in preceding papers [Ma, F. et al., World J Gastroenterol., 16(44), 5629-5634, 2010], [Xiao, Z. P. et al., J Agric Food Chem., 60(42), 10572-10577, 2012] and [Hyun-a, Lee, etc., Korean J Vet Res., 53(2), 117-123, 2013], there is disclosed an anti-*Helicobacter pylori* effect on various kinds of natural water extracts, including the *Lonicera japonica* flower extract. In addition, in the prior art [Oku, H. et al., Biol. Pharm. Bull., 34(8), 1330-1333, 2011], there are disclosed a *Lonicera japonica* flower-derived compound including secoxyloganin and an antiallergic effect thereof, and in the prior art [Xiong, J. et al., Food Chemistry, 138, 327-333, 2013], there is disclosed an antibacterial effect of secoxyloganin on *Escherichia coli* and *Staphylococcus aureus*.

The present inventors found that in active ingredients of the *Lonicera japonica* flower water extract, particularly, secoxyloganin exhibited a selective antibacterial effect of 20 times or more on *Helicobacter pylori* than the antibacterial effect on *Escherichia coli* and *Staphylococcus aureus* under the same condition, while studying the *Lonicera japonica* flower water extract. In addition, the present inventors found that the *Lonicera japonica* flower water extract containing a predetermined content or more of secoxyloganin had an excellent effect of suppressing and treating the infection of *Helicobacter pylori* and then completed the present invention.

DISCLOSURE

Technical Problem

It is an object of the present invention to provide a pharmaceutical composition or a health functional food for preventing or treating *Helicobacter pylori* infection comprising a *Lonicera japonica* flower water extract.

Technical Solution

The present invention relates to a pharmaceutical composition for preventing or treating *Helicobacter pylori* infection comprising secoxyloganin as an active ingredient, as a *Lonicera japonica* flower water extract.

The *Lonicera japonica* flower water extract may be obtained by mixing *Lonicera japonica* flower with 1500 to 2500 parts by weight of water with respect to 100 parts by weight of *Lonicera japonica* flower, and then extracting the mixture for 1 hour or more in a temperature condition of 90° C. or higher, and as an extraction device, a conventional extraction device, a sonication extractor, or a fraction device may be used. Preferably, the mixture was extracted for 1 to 5 hours in the temperature condition of 90° C. or higher to contain the active ingredient, secoxyloganin in 0.1 to 10 wt %.

The secoxyloganin contained as the active ingredient in the *Lonicera japonica* flower water extract is contained in 0.1 to 10 wt % in the *Lonicera japonica* flower water extract. When the content is less than 0.1 wt % or more than 10 wt %, beyond the range of wt %, it is not preferred in that an effect of inhibiting the infection to *Helicobacter pylori* is low or it is not preferred in that an increase of the effect of inhibiting the infection to *Helicobacter pylori* is not large and it is not economic. Most preferably, for effective treatment for *Helicobacter Pylori* Infection, the secoxyloganin contained as the active ingredient in the *Lonicera japonica* flower water extract is contained in 0.5 to 5 wt % in the *Lonicera japonica* flower water extract.

The *Helicobacter pylori* infection is a disease that is infected with *Helicobacter pylori* and may be selected from the group consisting of gastritis, gastric ulcer, duodenal ulcer, non-ulcer indigestion syndromes, gastric MALT lymphoma, gastric hyperplasia polyps, gastric cancer, digestive cancer, pancreatitis, inflammatory bowel disease, and functional digestive disorders (abdominal satiety, abdominal pain, burp, domperidone, initial satiety, nausea, vomiting, reflux, brash, loss of appetite, etc.). The *Lonicera japonica* flower water extract of the present invention exhibits a particularly selective therapeutic effect on *Helicobacter pylori* infectious diseases compared to *Helicobacter pylori* noninfectious diseases.

The pharmaceutical composition according to the present invention may be formulated in a suitable form with a pharmaceutically acceptable carrier which is commonly used. The "pharmaceutically acceptable" refers to a composition that is physiologically acceptable and does not cause an allergic reaction, such as gastrointestinal disorder, dizziness, etc., or a similar reaction thereto when administered to humans. In addition, the composition may be formulated and used in the form of oral formulations such as powders, granules, tablets, capsules, suspensions, emulsions, syrups, aerosols, etc., external preparations, suppositories, and sterile injectable solutions according to a general method.

Carriers, excipients, and diluents that may be included in the composition may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl p-hydroxybenzoate, propyl p-hydroxybenzoate, talc, magnesium stearate, and mineral oil, but are not limited thereto. The formulations may be prepared by using a diluent or an excipient, such as a filler, a stabilizer, a binder, a disintegrating agent, a surfactant, etc., which are commonly used. Solid formulations for oral administration include a tablet, a pill, a powder, a granule, a capsule, and the like, and these solid formulations may be prepared by mixing at least one or more excipients, for example, starch, microcrystalline cellulose, sucrose or lactose, low-substituted hydroxypropyl cellulose, hypromellose, and the like with at the extract of the present invention. Further, lubricants such as magnesium stearate and talc may also be used in addition to simple excipients. Liquid formulations for oral administration may correspond to suspensions, oral liquids, emulsions, syrups, and the like, and may include various excipients, for example, a wetting agent, a sweetener, an aromatic agent, a preservative, and the like, in addition to water and liquid paraffin which are commonly used as simple diluents. Formulations for parenteral administration include a sterile aqueous solution, a non-aqueous solution, a suspension, an emulsion, a lyophilizing agent, and a suppository. As the non-aqueous solution and the suspension, propylene glycol, polyethylene glycol, vegetable oil such as olive oil, injectable ester such as ethyl oleate, and the like may be used. As a base of the suppository, witepsol, macrogol, Tween 61, cacao butter, laurinum, glycerol, gelatin, and the like may be used. For preparation as formulations for parenteral administration, the extract or a pharmaceutically acceptable salt is sterilized and/or mixed with a preservative, a stabilizer, a wettable powder or emulsificant, an adjuvant such as salts and/or buffers for regulation of osmotic pressure, and other therapeutically useful materials in water to be prepared by a solution or suspension, and the prepared solution or suspension may be prepared by an ampoule or vial unit dose type.

The pharmaceutical composition comprising the extract disclosed in the present invention as an active ingredient may be administered to mammals such as rats, livestock, and human in various routes. All methods of administration may be expected and for example, the pharmaceutical composition may be administered by oral, rectal or intravenous, intramuscular, subcutaneous, intrauterine dural or cerebrovascular injection. A dose may vary according to the age, gender, and body weight of a subject to be treated, a specific disease or pathology to be treated, the severity of disease or pathology, an administration time, an administration route, the absorption of a drug, distribution and excretion rate, types of other drugs to be used, judgment of prescribers, etc. The dose determination based on these factors is within a level of those skilled in the art, and in general, the dose is in the range of 0.01 mg/kg/day to about 2000 mg/kg/day. A more preferable dose is 1 mg/kg/day to 500 mg/kg/day. The administration may be performed once a day or several times a day. The dose does not limit the scope of the present invention in any aspect.

In another aspect, the present invention relates to a health functional food for preventing or improving *Helicobacter pylori* infection comprising secoxyloganin as an active ingredient, as a *Lonicera japonica* flower water extract.

The health functional food refers to foods that are prepared or processed by using raw materials or components having useful functionality, and may include, for example, all of health supplements, functional foods, nutrients, adjuvants, and the like.

The extract may be added in preferably 0.001 wt % to 50 wt %, more preferably 0.001 wt % to 30 wt %, and most preferably 0.001 wt % to 10 wt %, with respect to the total weight of the entire health functional food. The health functional food of the present invention includes forms such as tablets, capsules, pills or liquids, and the like, and foods that may be added with the extract of the present invention include, for example, various foods, beverages, gum, tea, vitamin complexes, etc.

Further, the present invention relates to a pharmaceutical composition for preventing or treating *Helicobacter pylori* infection comprising secoxyloganin as an active ingredient.

Advantageous Effects

The present invention relates to a composition for preventing or treating *Helicobacter pylori* infection of a *Lonic-*

*era japonica* flower water extract containing secoxyloganin as an active ingredient. The extract contains a specific content of secoxyloganin, and thus exhibited excellent antibacterial effects when treated to *Helicobacter pylori* bacteria, and exhibited excellent effects in terms of reducing *Helicobacter pylori* IgG antibody expression in the blood, alleviating histopathological lesions, and reducing cytokine expression when treated to *Helicobacter pylori*-infected mice. Accordingly, the *Lonicera japonica* flower water extract of the present invention can be usefully used as a composition for preventing or treating *Helicobacter pylori* infection.

BEST MODE

Figure 1:
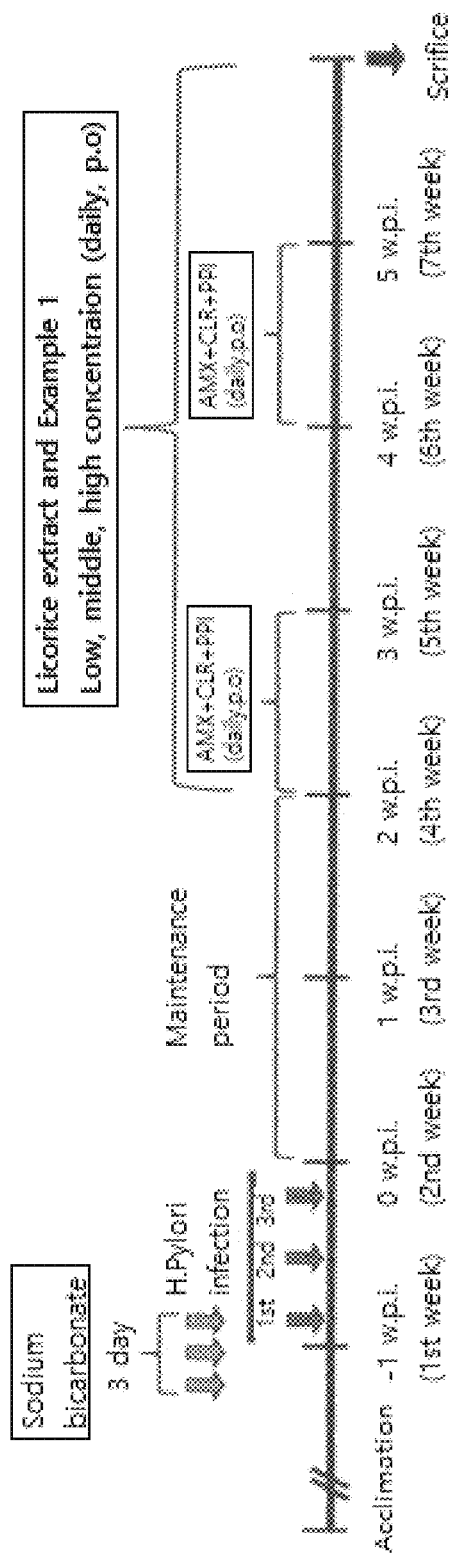
FIG. 1 illustrates a process of preparing *Helicobacter pylori*-infected mice.

Hereinafter, preferred Examples of the present invention will be described in detail. However, the present invention is not limited to Examples described herein and may also be embodied in other forms. Rather, the contents introduced here are to be thorough and complete, and provided to fully impart the spirit of the present invention to those skilled in the art.

Example 1. Preparation ① of *Lonicera japonica* Flower Water Extract 100 g of *Lonicera japonica* flower was added with 2000 ml of water and extracted with hot water at 90° C. for 3 hours to obtain 1400 ml of a *Lonicera japonica* flower extract. The extract was filtered through a filter paper of 5 μm, and then concentrated under reduced pressure for 3 hours at 50° C. Thereafter, the concentrate was dried under reduced pressure at 50° C. overnight to obtain 25 g of a *Lonicera japonica* flower water extract in Example 1 of the present invention.

Example 2. Preparation ② of *Lonicera japonica* Flower Water Extract 100 g of *Lonicera japonica* flower was added with 2000 ml of water and extracted with hot water at 90° C. for 1 hour to obtain 1400 ml of a *Lonicera japonica* flower extract. The extract was filtered through a filter paper of 5 μm, and then concentrated under reduced pressure for 3 hours at 50° C. Thereafter, the concentrate was dried under reduced pressure at 50° C. overnight to obtain 25 g of a *Lonicera japonica* flower water extract in Example 2 of the present invention.

Example 3. Preparation (of *Lonicera japonica* Flower Water Extract 100 g of *Lonicera japonica* flower was added with 2000 ml of water and extracted with hot water at 90° C. for 5 hours to obtain 1400 ml of a *Lonicera japonica* flower extract. The extract was filtered through a filter paper of 5 μm, and then concentrated under reduced pressure for 3 hours at 50° C. Thereafter, the concentrate was dried under reduced pressure at 50° C. overnight to obtain 25 g of a *Lonicera japonica* flower water extract in Example 3 of the present invention.

Comparative Example 1. Preparation of *Lonicera japonica* Flower Ethanol Extract to be Compared In the same manner as in Example 1, a *Lonicera japonica* flower ethanol extract of Comparative Example 1 was prepared by using a 70 ethanol aqueous solution instead of water as an extract solvent.

Comparative Example 2. Preparation ① of *Lonicera japonica* Flower Water Extract to be Compared In the same manner as in Example 1, a *Lonicera japonica* flower water extract of Comparative Example 2 was prepared by extraction for 3 hours at 60° C. instead of hot-water extraction for 3 hours at 90° C.

Comparative Example 3. Preparation ② of *Lonicera japonica* Flower Water Extract to be Compared In the same manner as in Example 1, a *Lonicera japonica* flower water extract of Comparative Example 3 was prepared by extraction for 3 hours at 30° C. instead of hot-water extraction for 3 hours at 90° C.

Comparative Example 4. Preparation ③ of *Lonicera japonica* Flower Water Extract to be Compared In the same manner as in Example 1, a *Lonicera japonica* flower water extract of Comparative Example 4 was prepared by extraction for 30 minutes at 90° C. instead of hot-water extraction for 3 hours at 90° C.

Experimental Example 1. Confirmation of Index Ingredient Content Contained in *Lonicera japonica* Flower Extract A standard solution was first prepared to confirm the content of an index ingredient contained in a *Lonicera japonica* flower extract. The standard solution was added with about 5 mg of a secoxyloganin standard product in a 50 ml flask and added with water and completely dissolved by sonication, and then the flask was cooled, and a solution adjusted to a marked line was used as a secoxyloganin solution at a high concentration (0.1 mg/ml).

Next, Examples and Comparative Examples were taken by about 200 mg, respectively, added in a 50 ml flask, added with water and completely dissolved by sonication, and the flask was cooled and adjusted to a marked line, and then a filtrate filtered with a membrane filter having a pore diameter of 0.22 μm was used as a test solution (4 mg/ml).

The HPLC performance conditions of the standard product, Examples, and Comparative Examples were shown in Table 1 below, and the contents of secoxyloganin among index ingredients contained in Examples and Comparative Examples were shown in Table 2 below.

TABLE 1

| | HPLC performance conditions |
|---|---|
| Column | INNO C18 250 mm × 4.6 mm, 3 μm Equivalent column thereto |
| Detection wavelength | 240-327 nm |
| Injection amount | 10 μl |
| Column temperature | 25° C. |
| Autosampler temperature | 10° C. |
| Flow rate | 0.8 ml/min. |
| Solvent | A: Phosphoric acid/water. B:Acetonitrile 0 Min: 81% A, 19% B; 13 Min.: 80% A, 20% B; 15 Min.: 75% A, 25% B; 35 Min.: 75% A, 25% B; 36 Min.: 10% A, 90% B; 44.5 Min.: 10% A, 90% B; 45 Min.: 81% A, 19% B; 55 Min.: 81% A, 19% B; |

TABLE 2

| | Secoxyloganin (mg/g) |
|---|---|
| Example 1 | 9.4 |
| Example 2 | 8.7 |
| Example 3 | 10.5 |
| Comparative Example 1 | 4.4 |
| Comparative Example 2 | 3.2 |
| Comparative Example 3 | 2.1 |
| Comparative Example 4 | 4.5 |

As shown in Table 2, it could be seen that the *Lonicera japonica* flower water extract in Examples of the present invention had a high content of secoxyloganin when the extraction temperature was 90° C. or higher.

Experimental Example 2. Confirmation of Antibacterial Activity on *Helicobacter pylori*

A *Helicobacter pylori* (ATCC43504) strain was smeared in a *Brucella* Agar medium containing 10% horse serum, and cultured for 3 days in an incubator of 37° C. and 10% CO: conditions. Thereafter, the cultured *Helicobacter pylori* cells were collected and then suspended in a sterilized *Brucella* liquid medium and a cell suspension having absorbance of 1.0 was prepared at 600 nm.

14 g of the *Brucella* medium was dissolved in 450 ml of purified water, added with 6 g of agar, suspended and sterilized at 121° C. for 15 minutes. 50 ml of horse serum was mixed in a sterilized medium at about 40° C., and dispensed on a plate having a diameter of 90 mm by 25 ml, and the agar medium was hardened, and then 0.2 ml of the *Helicobacter pylori* cell suspension was smeared on the agar medium.

The Examples and Comparative Examples were dissolved in water by concentration and sterilized and filtered at 0.2 μm, and then treated on a sterile paper disc (diameter of 6 mm) by 20 μl, respectively, and placed on a plate smeared with the strain. The Examples and Comparative Examples were cultured for 72 hours in an incubator of 37° C. and 10% CO: conditions, and then diameters of generated clear zones were measured and diameters of pure inhibition zones removing perforated diameters were shown in Table 3.

TABLE 3

| Treatment condition | | Clear zone (mm) |
|---|---|---|
| Example 1 | 100 mg/ml | 13 |
| Example 2 | 100 mg/ml | 10 |
| Example 3 | 100 mg/ml | 14 |
| Comparative Example 1 | 100 mg/ml | 7 |
| Comparative Example 2 | 100 mg/ml | 5 |
| Comparative Example 3 | 100 mg/ml | 4 |
| Comparative Example 4 | 100 mg/ml | 5 |
| Secoxyloganin | 0.1 mg/ml | 5 |
| | 1 mg/ml | 9 |
| | 10 mg/ml | 13 |
| Untreated group (distilled water) | | 0 |

As can be seen through Table 3 above, it could be seen that when the *Lonicera japonica* flower water extract in Examples 1 to 3 containing 0.5 wt % or more of secoxyloganin as an index ingredient was treated to *Helicobacter pylori*, clear zones of 10 mm or more were shown to have excellent antibacterial activity.

Particularly, the present inventors confirmed an effect of inhibiting *Helicobacter pylori* infection in mice by oral administration of 100 mg/kg using the *Lonicera japonica* flower water extract depending on the content of secoxyloganin, respectively. As a result, unlike Comparative Examples 1 to 4, it was confirmed that only in the *Lonicera japonica* flower water extracts containing 0.5 wt % or more of secoxyloganin in Examples 1 to 3, the effect of inhibiting the *Helicobacter pylori* infection was exhibited. Accordingly, thereafter, in an animal experiment, it was confirmed that the effect of inhibiting the *Helicobacter pylori* infection was exhibited by oral administration of the composition of Example 1 to *Helicobacter pylori*-infected mice depending on doses of 100 mg/kg, 200 mg/kg, and 400 mg/kg.

Experimental Example 3. Confirmation of Effect of Inhibiting *Helicobacter pylori* Infection Experimental Example 3-1. Preparation of *Helicobacter pylori*-Infected Mice First, a *Helicobacter pylori* strain (*H. pylori* SS1, Korea Helicobacter Bank) was inoculated in a trypticase soy agar medium added with 5% sheep blood and then cultured for 2 to 3 days under 10% $CO_2$, 37° C., and micro-aerobic conditions.

To increase the infection rate of *Helicobacter pylori*, an antiacid was administrated to mice before 2 days of *Helicobacter pylori* infection and on the infection day, and in all groups, 5% sodium bicarbonate ($NaHCO_3$) was orally administrated using a mouse zonde by 0.2 ml per mouse once for total 3 days.

Mice before *Helicobacter pylori* infection were fasted for 12 hours, and in all groups except for a negative control group G1, a *Helicobacter pylori* culture solution was orally administrated and infected at intervals of 2 days by 0.2 ml using the mouse zonde according to the bacterial count of 5.0×10⁹/ml colony-forming unit (CFU).

To confirm the infection maintenance after induction of *Helicobacter pylori* infection, after 1 week of the *Helicobacter pylori* infection, the blood was collected from the facial vein of all mice and the plasma was isolated. In the *Helicobacter pylori* antibody measurement, only individuals in which the increased antibody by the infection was identified were selected by a Mouse *H. pylori* antibody (IgG) ELISA Kit (Cusabio Biotech Co., USA) and used in the test.

All test groups were suspended in distilled water and orally administrated by 5 ml per mouse 1 kg at the same time every day and administered for 28 days, once a day (in a positive control group 1, 1 week, 3 weeks, once a day, 14 days).

TABLE 4

| Cause of disease | Conditions | Dose (ml/kg) |
|---|---|---|
| PBS | Normal group (untreated group, D.W. G1) | 5 |
| H. pylori | Infected group (untreated group, D.W. G2) | 5 |
| | Positive group 1 (AMX + CLR + PPI (omeprazole), G3) | 5 |
| | Positive group 2 (Licorice extract 60 mg/kg, G4) | 5 |
| | Example 1 (100 mg/kg, G5) | 5 |
| | Example 1 (200 mg/kg, G6) | 5 |
| | Example 1 (400 mg/kg, G7) | 5 |

Experimental Example 3-2. PCR Test of Helicobacter pylori in Gastric Mucosal Membrane Genomic DNA was collected from the gastric mucosal tissue extracted aseptically, and a PCR test of *Helicobacter pylori* was performed under conditions of Table 5 below. A target gene used in the experiment was CagA, which was a toxic gene present specifically only in *Helicobacter pylori*, as a gene that was not present in humans or mice. Accordingly, FIG. 2 illustrated that in *Helicobacter pylori*-infected mice, specific bands generated by treating each test group were identified and positive individuals were determined.

TABLE 5

| PCR performance condition | | |
|---|---|---|
| Primer | H-cagA-F(5'-ATAATGCTAAATTAGACAACTTGAAGCGA) (SEQ ID NO: 1) H-cagA-R(5'-TTAGAATAATCAACAAACATCACGCCAT) (SEQ ID NO: 2) | |
| Reaction condition | Denaturation at 94° C. for 5 min. | 298 bp |
| | 95° C for 1 min | 35 cycles |
| | 57° C for 30 s | |
| | 72° C for 30 s | |
| | Final extension step 72° C for 10 min | |

Figure 2:
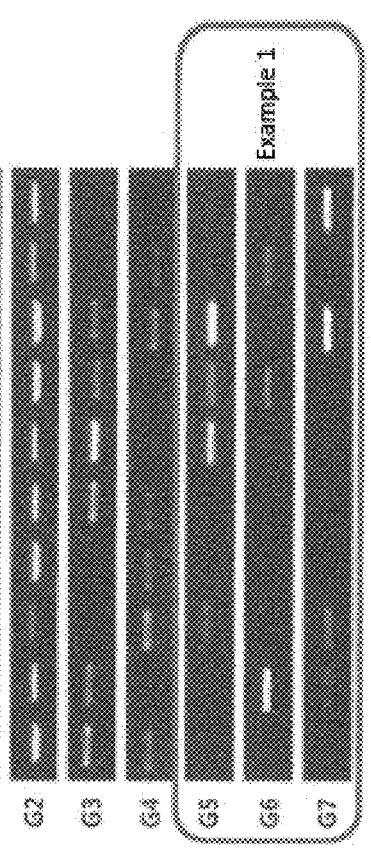
FIG. 2 illustrates a result of confirming the presence of *Helicobacter pylori* in the gastric mucosal tissue by PCR according to administration of a *Lonicera japonica* flower extract to *Helicobacter pylori*-infected mice.

FIG. 2 illustrated that as a result of measuring the presence of *Helicobacter pylori* in the gastric mucosal tissue by PCR and calculating a treatment rate of each test group, *Lonicera japonica* flower extracts G5 to G7 in Example 1 of the present invention exhibited the treatment rate of 40 to 60% as compared with an infected group G2 for each concentration. Accordingly, it could be seen that the *Lonicera japonica* flower extract of the present invention was a composition for reducing the expression of the specific gene in the gastric mucosal membrane which was increased by the *Helicobacter pylori* infection.

Experimental Example 3-3. Comparison of Helicobacter pylori Antibody IgG Titers in Blood In Experimental Example 3-1, in the plasma isolated from the mouse facial vein after 1 week of the induction of *Helicobacter pylori* infection and the plasma isolated after collecting the blood from the abdominal vein at the end of the experiment, a *Helicobacter pylori* antibody titer in each plasma was measured by a Mouse *H. pylori* antibody (IgG) ELISA Kit and illustrated in FIG. 3.

Figure 3:
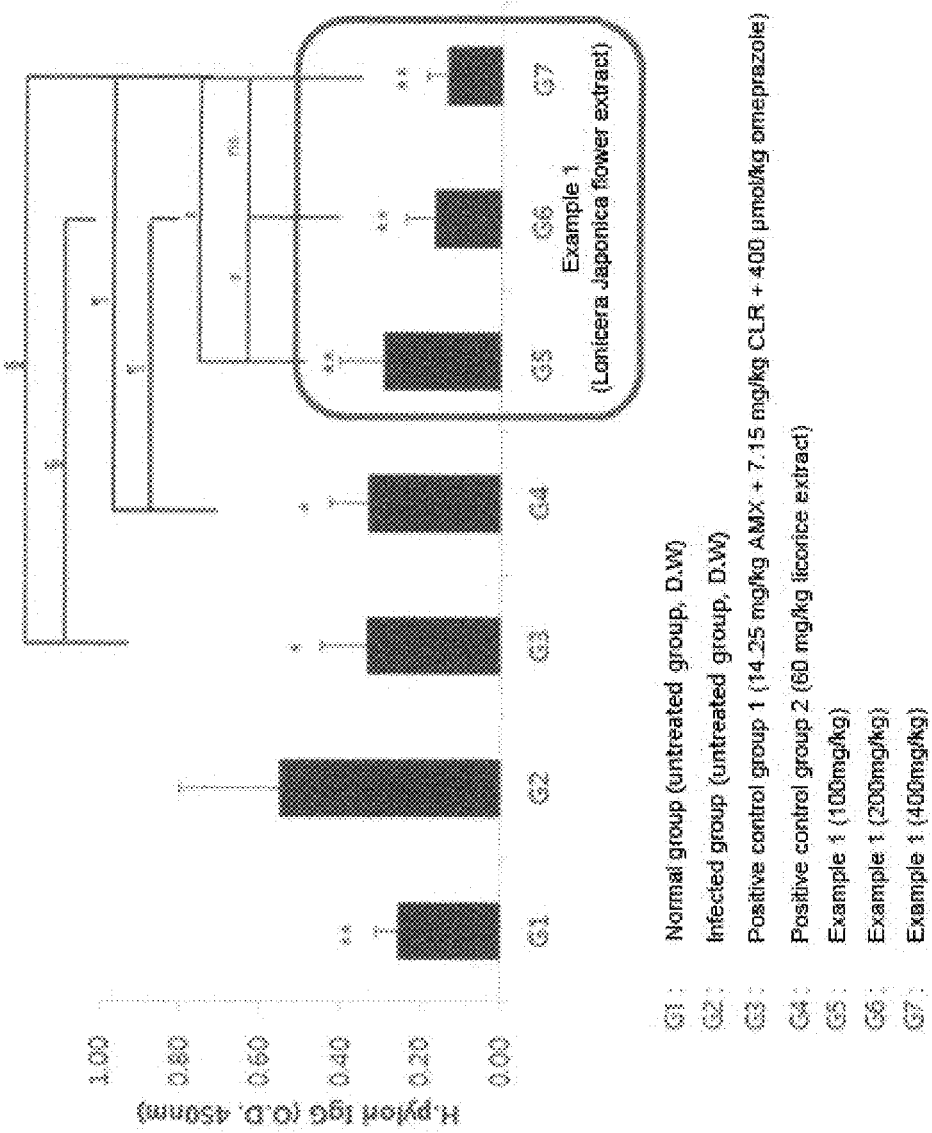
FIG. 3 illustrates a result of confirming the *Helicobacter pylori* IgG antibody expression in the blood according to administration of a *Lonicera japonica* flower extract to *Helicobacter pylori*-infected mice.

In FIG. 3, as a result of measuring the *Helicobacter pylori* antibody in the blood during autopsy, it could be seen that in Examples G5 to G7 of the present invention, the *Helicobacter pylori* antibody was decreased in a concentration-dependent manner as compared with the infected group G2.

Through this, it could be seen that the *Lonicera japonica* flower water extract of the present invention comprising the secoxyloganin as the active ingredient was a composition having an excellent effect of inhibiting the infection by *Helicobacter pylori*.

Experimental Example 3-4. Observation of Visible Lesions in Gastric Tissue and Comparison of Histopathological Analysis The gastric tissue extracted on the autopsy day was cut and opened in a vertical direction toward the duodenum from the esophagus along the great curvature and a specific lesion of the inner mucosal membrane was observed. After the observation of the visible lesion, the opened gastric tissue was immobilized in 10% j neutral formalin, paraffin-embedded using a general method for a histopathological test, and then sliced to 4 μm thick, and stained by hematoxylin and eosin (H&E), and thereafter, a histopathological test was performed. The histopathological scores were illustrated in FIG. 4 by converting a grade of each tissue to scores, after observing the infiltration degree (marked with a yellow arrow) of inflammatory cells (neutrophils & mononuclear cells) and the degree of atrophic gastritis accompanying atrophic change which were comprehensively shown in Corpus and Antrum overall regions per individual according to criteria of Table 6.

TABLE 6

| Parameter | Score | Criteria |
|---|---|---|
| Inflammation | 0 | No lymphocytic or granulocytic infiltration |
| | 1 | Mild mucosel lymphocytic infiltration |
| | 2 | Moderate mucosal lymphocytic infiltration, some multifocal mucosal lymphoid aggregates |
| | 3 | Extensive multifocal mucosal lymphoid aggregates |
| | 4 | Multifocal mucosal and submucosal lymphoid aggregates |
| Atrophic gastritis | 0 | Parietal cells and glandular architecture preserved |
| | 1 | Minimal parietal cell loss, glandular architecture preserved |
| | 2 | Moderate arietal cell loss, glandular architecture preserved |
| | 3 | Significant parietal cell loss, glandular branching and hyperplasia |
| | 4 | Significant parietal cell loss, glandular branching and hyperplasia with submucosal gladular herniation |

Figure 4:
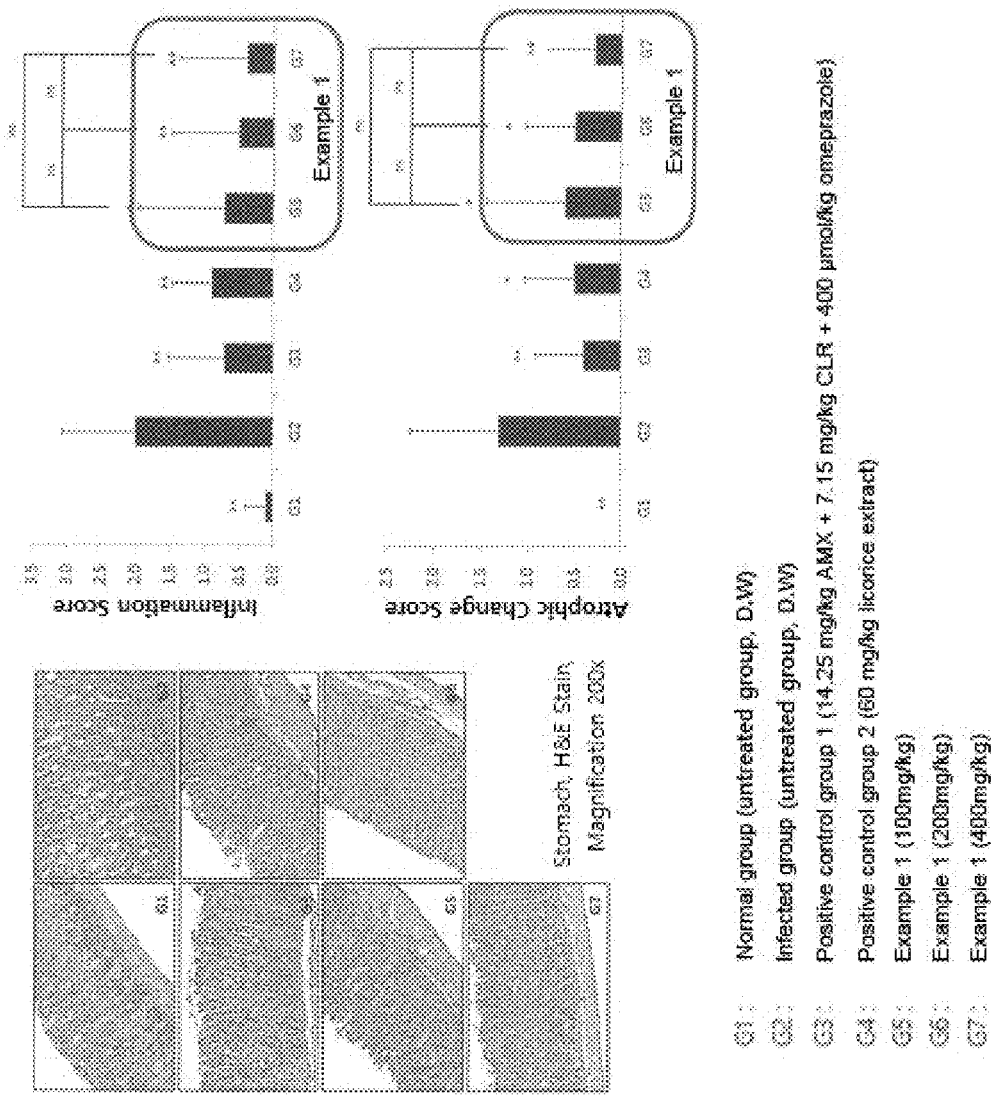
FIG. 4 illustrates a result of scoring inflammatory cell infiltration and atrophic change in the gastric tissue according to administration of a *Lonicera japonica* flower extract to *Helicobacter pylori*-infected mice.

Referring to FIG. 4, the findings observed in the gastric tissue as the histopathological result were scored with respect to inflammatory cell infiltration and atrophic change according to criteria of Prior Art [Lee, J. Y. et al., J Cancer Prev., 19(2), 144-151, 2014]. In the infected group G2, the inflammation in the gastric tissue and the atrophic change were increased by the *Helicobacter pylori* infection as compared with a normal group, but in Examples G5 to G7, the inflammation in the gastric tissue and the atrophic change were decreased in a concentration-dependent manner.

Through this, it could be seen that the *Lonicera onicera Lonicera japonica* flower extract of the present invention reduced gastritis symptoms by inflammatory cell infiltration and atrophic change at the time of *Helicobacter pylori* infection.

Experimental Example 3-5. Rapid Urease Test (CLO Test)

When *Helicobacter pylori* was present in the gastric mucosal membrane, while the *Helicobacter pylori* was proliferated in a test reagent medium, urease was secreted and urea in the test reagent was hydrolyzed to produce ammonia. As a result, the total pH of the test reagent was increased, and a rapid urease test was performed from a color change (red) of this pH indicator, and the test result was represented by the treatment rate and CLO scores.

In the rapid urease test, the gastric mucosal membrane extracted on the autopsy day was aseptically collected and tested by using a *campylobacter*-like organism (CLO) (Asan Pharm Co., Ltd., Korea) as a test reagent. The collected gastric mucosal membrane was cultured in an incubator at 37° C. for 2 hours and then was determined as positive when the reagent color was changed from yellow to red. The number of individuals determined by positive was obtained by the percentage to calculate a positive rate, and the treatment rate for *Helicobacter pylori* sterilization by a sample treatment was calculated by the following Equation and illustrated in FIG. 5.

$$\{(\text{the number of samples} - \text{the number of positive samples})/\text{the number of samples}\} \times 100 \quad [\text{Equation}]$$

Figure 6:
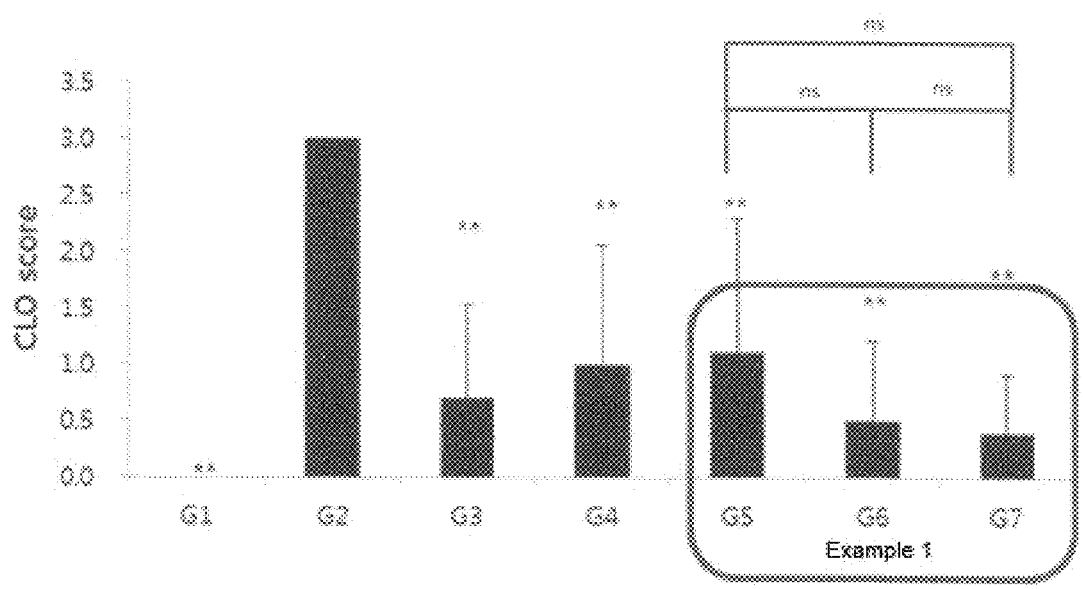
FIG. 6 illustrates a result of confirming CLO scores according to administration of a *Lonicera japonica* flower extract to *Helicobacter pylori*-infected mice.

Further, after the CLO test, the CLO scores were illustrated in FIG. 6 by measuring Score 0 in the case of no change in color of the medium, Score 1 in the case of slight red, Score 3 in the case of light purple, and Score 3 in the case of dark purple, calculating the average and standard deviation of each group and comparing differences between the groups.

Figure 5:
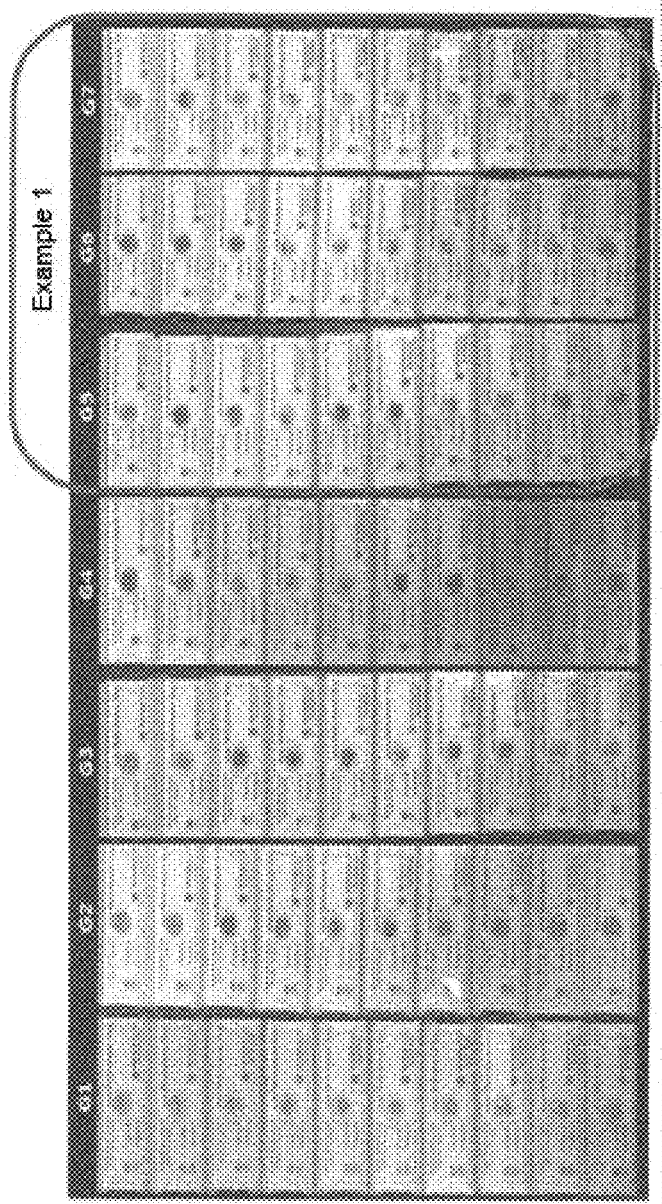
FIG. 5 illustrates a result of a rapid urease test according to administration of a *Lonicera japonica* flower extract to *Helicobacter pylori*-infected mice.

When describing the treatment rate and the CLO score result by the rapid urease test of FIGS. 5 and 6, the *Lonicera japonica* flower extracts G5 to G7 in Example 1 of the present invention exhibited the treatment rate of 40 to 60% as compared with the infected group G2, and exhibited an effect of reducing the CLO score of 60 to 90%.

Accordingly, it could be seen that the *Lonicera japonica* flower extract of the present invention was a composition for reducing the expression of the rapid urease in the gastric mucosal membrane which was increased by the *Helicobacter pylori* infection.

Experimental Example 3-6. Cytokine Analysis in Gastric Mucosal Tissue

To measure pro-inflammatory cytokines in the gastric mucosal tissue, the gastric tissue aseptically collected was pulverized with liquid nitrogen and proteins were extracted using a cell lysis buffer to be used for analysis. In the isolated proteins, tumor necrosis factor-$\alpha$ (TNF-$\alpha$) and Interleukin-1$\beta$ (IL-1$\beta$) were analyzed using an ELISA kit (R&D system, Minneapolis, MN, USA) and the result thereof was illustrated in FIG. 7.

Figure 7:
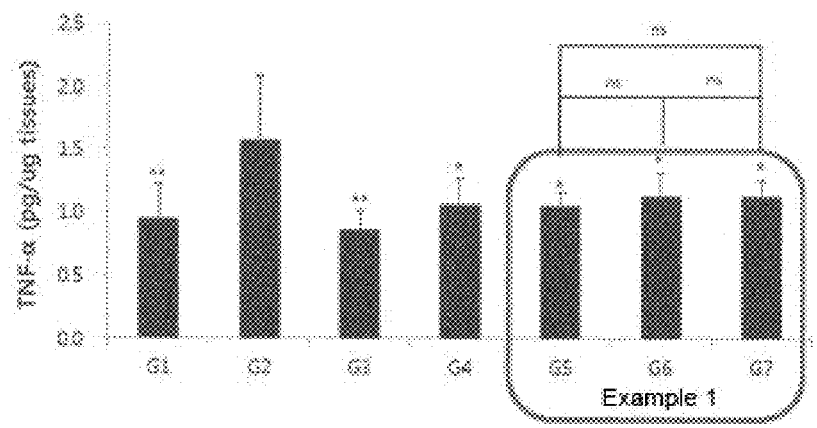
FIG. 7 illustrates a result of measuring expression levels of TNF-α and IL-1β in the gastric mucosal tissue according to administration of a *Lonicera japonica* flower extract to *Helicobacter pylori*-infected mice.
Figure 7:
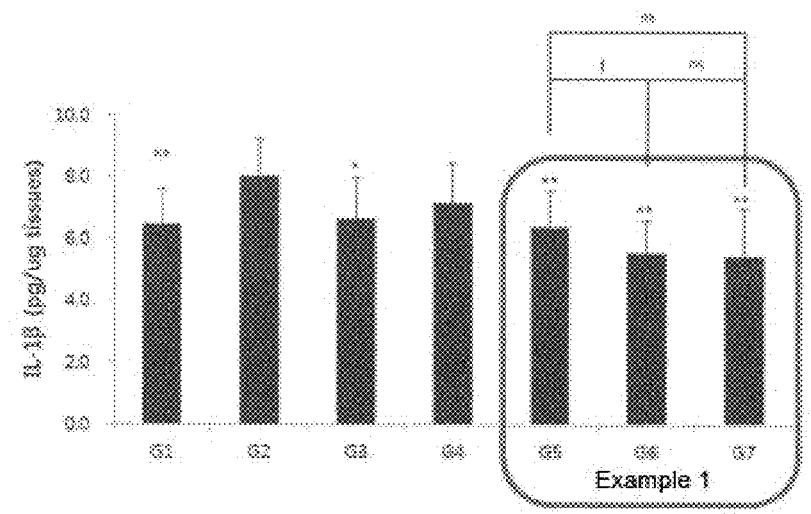

Referring to FIG. 7, the *Lonicera japonica* flower extract of Example 1 of the present invention reduced the expression of TNF-$\alpha$ and IL-1$\beta$ in the gastric mucosal tissue increased by *Helicobacter pylori* infection in a concentration-dependent manner.

Preparation Example 1. Preparation of Tablets 20 g of the *Lonicera japonica* flower extract in Example 1 of the present invention was mixed with 175.9 g of lactose, 180 g of potato starch and 32 g of colloidal silicate. The mixture was added with a 10% gelatin solution and then pulverized and passed through a 14 mesh body. This mixture was dried and added with 160 g of potato starch, 50 g of talc, and 5 g of magnesium stearic acid to prepare tablets.

Preparation Example 2. Preparation of Capsules 100 mg of the *Lonicera japonica* flower extract in Example 1 of the present invention, 100 mg of corn starch, 100 mg of lactose, and 2 mg of magnesium stearic acid were mixed and then the ingredients were mixed according to a general preparation method of capsules and filled in capsules to prepare capsules.

Preparation Example 3. Preparation of Injections 1 g of the *Lonicera japonica* flower extract in Example 1 of the present invention, 0.6 g of sodium chloride and 0.1 g of ascorbic acid were dissolved in distilled water to make 100 ml. This solution was placed in a bottle and heated and sterilized at 20° C. for 30 minutes.

Preparation Example 4. Preparation of Health Functional Foods 20 g of the *Lonicera japonica* flower extract in Example 1 of the present invention, a suitable amount of vitamin mixture, vitamin A acetate 70 µg, vitamin E 1.0 mg, vitamin B1 0.13 mg, vitamin B2 0.15 mg, vitamin B6 0.5 mg, vitamin B12 0.2 µg, vitamin C 10 mg, biotin 10 µg, nicotinicamide 1.7 mg, folic acid 50 µg, calcium pantothenate 0.5 mg, a suitable amount of mineral mixture, ferrous sulfate 1.75 mg, zinc oxide 0.82 mg, magnesium carbonate 25.3 mg, mono potassium phosphate 15 mg, dicalcium phosphate 55 mg, potassium citrate 90 mg, calcium carbonate 100 mg, and magnesium chloride 24.8 mg were mixed to prepare granules, but may be variously modified and prepared into various formulations according to the use. In addition, the composition ratio of the vitamins and mineral mixtures may be arbitrarily modified, and the foods may be prepared by mixing the above ingredients according to a general preparation method of health functional foods.

Preparation Example 5. Preparation of Health Functional Drinks 1 g of the *Lonicera japonica* flower extract in Example 1 of the present invention, 0.1 g of citric acid, 100 g of fructooligosaccharide, and 900 g of purified water were mixed and stirred, heated, filtered, sterilized, and refrigerated according to a general preparation method of drinks to prepare drinks.

The invention claimed is:

1. A method for treating *Helicobacter pylori* infection in a subject in need thereof, comprising administering an effective amount of a composition comprising *Lonicera japonica* flower water extract or secoxyloganin as an active ingredient, to the subject, wherein the *Lonicera japonica* flower water extract contains secoxyloganin,
wherein the secoxyloganin is contained in 0.5 to 5 wt % in the *Lonicera japonica* flower water extract, and
wherein the *Lonicera japonica* flower water extract is obtained by mixing *Lonicera japonica* flower with 1500 to 2500 parts by weight of water with respect to 100 parts by weight of *Lonicera japonica* flower, and then extracting a resulting mixture for 1 to 5 hours at a temperature of 90° C.

2. The method of claim 1, wherein the composition is a pharmaceutical composition or a foodstuff.

3. The method of claim 2, wherein the pharmaceutical composition further comprises a pharmaceutically acceptable carrier, an excipient or a diluent.

4. The method of claim 2, wherein the foodstuff is in a form of a tablet, a capsule, a pill, or a liquid.

* * * * *